US00PP23214P2

(12) United States Plant Patent
Moore

(10) Patent No.: US PP23,214 P2
(45) Date of Patent: Nov. 27, 2012

(54) BUDDLEJA PLANT NAMED 'PINK PAGODA'

(50) Latin Name: *Buddleja weyeriana×Buddleja davidii*
Varietal Denomination: Pink Pagoda

(75) Inventor: Peter Moore, Stockbridge (GB)

(73) Assignee: Spring Meadow Nursery, Inc., Grand Haven, MI (US)

( * ) Notice: Subject to any disclaimer, the term of this patent is extended or adjusted under 35 U.S.C. 154(b) by 98 days.

(21) Appl. No.: 13/065,262

(22) Filed: Mar. 18, 2011

(51) Int. Cl.
*A01H 5/00* (2006.01)

(52) U.S. Cl. ..... Plt./242

(58) Field of Classification Search ..... Plt./242
See application file for complete search history.

(56) References Cited

PUBLICATIONS

Kimberley. Buddleja. Horticulture Week Aug. 2009, retrieved on Aug. 15, 2012. Retrieved from the Internet at <http://www.hortweek.com/news/929514/buddleja/> pp. 1-5.*
Moore. Passion an long-term commitment. The Plantsman Sep. 2010, pp. 198-201.*
Pluto:Plant Variety Database 2012-03, UPOV, retrieved on Aug. 14, 2012. Retrieved from <http://www.upov.int/pluto/en/index.jsp>, one page.*

* cited by examiner

*Primary Examiner* — June Hwu
(74) *Attorney, Agent, or Firm* — C. A. Whealy

(57) ABSTRACT

A new and distinct cultivar of *Buddleja* plant named 'Pink Pagoda', characterized by its upright, outwardly spreading and mounding plant habit; continuous flowering habit; long narrowly conical inflorescences with numerous pink-colored flowers; and good garden performance.

2 Drawing Sheets

Botanical designation: *Buddleja weyeriana×Buddleja davidii.*

Cultivar denomination: 'PINK PAGODA'.

BACKGROUND OF THE INVENTION

The present invention relates to a new and distinct cultivar of *Buddleja* plant, botanically known as *Buddleja weyeriana×Buddleja davidii* and hereinafter referred to by the name 'Pink Pagoda'.

The new *Buddleja* plant is a product of a planned breeding program conducted by the Inventor in Longstock, Stockbridge, United Kingdom. The objective of the breeding program was to create new *Buddleja* plants with continuous flowering and attractive flower coloration.

The new *Buddleja* plant originated from a cross-pollination conducted by the Inventor in 1994 in Longstock, Stockbridge, United Kingdom, of *Buddleja weyeriana* 'Sungold', not patented, as the female, or seed, parent with *Buddleja davidii* 'Pink Delight', not patented, as the male, or pollen, parent. The new *Buddleja* plant was discovered and selected by the Inventor as a single flowering plant within the progeny of the stated cross-pollination in a controlled environment in Longstock, Stockbridge, United Kingdom in 1997.

Asexual reproduction of the new *Buddleja* plant by softwood cuttings in a controlled environment in Longstock, Stockbridge, United Kingdom since 1997 has shown that the unique features of this new *Buddleja* plant are stable and reproduced true to type in successive generations.

SUMMARY OF THE INVENTION

Plants of the new *Buddleja* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Pink Pagoda'. These characteristics in combination distinguish 'Pink Pagoda' as a new and distinct *Buddleja* plant:

1. Upright, outwardly spreading and mounding plant habit.
2. Continuous flowering habit.
3. Long narrowly conical inflorescences with numerous pink-colored flowers.
4. Good garden performance.
5. Flowers do not produce pollen or seeds.

Plants of the new *Buddleja* differ primarily from plants of the female parent, 'Sungold' in the following characteristics:

1. Plants of the new *Buddleja* have conical inflorescences whereas plants of 'Sungold' have globose inflorescences.
2. Plants of the new *Buddleja* and 'Sungold' differ in flower color as plants of 'Sungold' have orange yellow-colored flowers.
3. Plants of the new *Buddleja* do not produce seeds whereas plants of 'Sungold' produce seeds.

Plants of the new *Buddleja* differ primarily from plants of the male parent, 'Pink Delight' in the following characteristics:

1. Plants of the new *Buddleja* and 'Pink Delight' differ in flower color as plants of 'Pink Delight' have bright pink-colored flowers.
2. Plants of the new *Buddleja* do not produce seeds whereas plants of 'Pink Delight' produce seeds.

Plants of the new *Buddleja* can be compared to plants of *Buddleja davidii* 'Orchid Beauty', not patented. In side-by-side comparisons, plants of the new *Buddleja* and 'Orchid Beauty' differed in the following characteristics:

1. Plants of the new *Buddleja* and 'Orchid Beauty' differed in flower color as plants of 'Orchid Beauty' had lavender-colored flowers.
2. Plants of the new *Buddleja* did not produce seeds whereas plants of 'Orchid Beauty' produce seeds.

Plants of the new *Buddleja* can also be compared to plants of *Buddleja weyeriana* 'Honeycomb', not patented. In side-by-side comparisons, plants of the new *Buddleja* and 'Honeycomb' differed in the following characteristics:

1. Plants of the new *Buddleja* were more uniform in plant shape than plants of 'Honeycomb'.
2. Plants of the new *Buddleja* and 'Honeycomb' differed in flower color as plants of 'Honeycomb' had yellow-colored flowers.

BRIEF DESCRIPTION OF THE PHOTOGRAPHS

The accompanying colored photographs illustrate the overall appearance of the new *Buddleja* plant showing the colors as true as it is reasonably possible to obtain in colored reproductions of this type. Colors in the photographs may differ slightly from the color values cited in the detailed botanical description which accurately describe the colors of the new *Buddleja* plant.

The photograph on the first sheet comprises a side perspective view of a typical flowering plant of 'Pink Pagoda' grown in an outdoor nursery.

The photograph on the second sheet is a close-up view of a typical inflorescence of 'Pink Pagoda'.

DETAILED BOTANICAL DESCRIPTION

The aforementioned photographs and following observations, measurements and values describe plants grown during the summer and early autumn in ground beds in an outdoor nursery in Grand Haven, Mich. and under commercial practice. Plants were pinched one time eight months apart and were 2.5 years old when the photographs and description were taken. In the following description, color references are made to The Royal Horticultural Society Colour Chart, 1995 Edition, except where general terms of ordinary dictionary significance are used.

Botanical classification: *Buddleja* hybrid 'Pink Pagoda'.

Parentage:

*Female, or seed, parent.*—*Buddleja weyeriana* 'Sungold', not patented.

*Male, or pollen, parent.*—*Buddleja davidii* 'Pink Delight', not patented.

Propagation:

*Type*.—By softwood cuttings.

*Time to initiate roots plant, summer*.—About 10 days at 24° C.

*Time to produce a rooted plant, summer*.—About two months at 24° C.

*Root description*.—Fine, fibrous; white in color.

*Rooting habit*.—Freely branching.

Plant description:

*Plant form/habit*.—Deciduous perennial shrub; upright, outwardly spreading and mounding plant habit; very broad inverted triangle; vigorous growth habit.

*Plant height*.—About 1 meter.

*Plant width* (*spread*).—About 1.6 meters.

*Lateral branches*.—Quantity: About 89 lateral branches develop per plant. Length: About 42 cm. Diameter: About 4 mm. Internode length: About 6 cm. Strength: Moderately strong to strong. Aspect: Erect to about 45° from vertical. Texture, developing stems: Slightly pubescent. Texture, mature stems: Smooth, glabrous. Color, developing: Close to 144B. Color, mature: Close to 166B.

Foliage description:

*Arrangement*.—Opposite, simple.

*Length*.—About 16 cm.

*Width*.—About 3.5 cm.

*Shape*.—Narrowly lanceolate.

*Apex*.—Acute to acuminate.

*Base*.—Cuneate to attenuate.

*Margin*.—Serrulate.

*Texture, upper surface*.—Smooth, glabrous.

*Texture, lower surface*.—Pubescent.

*Venation pattern*.—Pinnate.

*Color*.—Developing leaves, upper surface: Close to 141B. Developing leaves, lower surface: Close to 190B. Fully expanded leaves, upper surface: Close to 139A; venation, close to 144A. Fully expanded leaves, lower surface: Close to 191A; venation, close to 137A.

*Petiole*.—Length: About 5 mm. Diameter: About 2 mm. Texture, upper and lower surfaces: Pubescent. Color, upper and lower surfaces: Close to 144A.

Flower description:

*Flower type and flowering habit*.—Single salverform flowers arranged on terminal panicles; flowers face upright and outwardly; panicles long and narrowly conical in shape; freely flowering habit with about 335 flowers per inflorescence.

*Fragrance*.—Fragrant; sweet, pleasant.

*Natural flowering season*.—Plants flower continuously from August to October in Michigan.

*Postproduction longevity*.—Flowers last about seven to ten days on the plant; flowers not persistent.

*Flower buds*.—Height: About 5 mm. Diameter: About 2.5 mm. Shape: Oblong. Color: Close to 146B.

*Inflorescence length*.—About 24 cm.

*Inflorescence diameter*.—About 5.5 cm.

*Flower diameter*.—About 7 mm.

*Flower depth*.—About 1.1 cm.

*Petals*.—Quantity per flower: Typically four in a single whorl; petals fused into a narrow tube. Lobe length: About 3 mm. Lobe width: About 4 mm. Shape: Roughly reniform. Apex: Broadly obtuse. Margin: Entire; undulate. Texture, upper and lower surfaces: Smooth, glabrous. Color: Developing petals, upper and lower surfaces: Close to 74C. Fully expanded petals, upper surface: Close to 75C; venation, close to 75C; color becoming closer to 75B with development. Fully expanded petals, lower surface: Close to 74C venation, close to 74C. Throat: Close to 25A; venation, close to 25A. Tube: Close to 74C; venation, close to 74C.

*Sepals*.—Quantity per flower: Typically four in a single whorl, fused towards the base into a short tube. Length: About 1 mm. Width: About 1 mm. Shape: Lanceolate. Apex: Acute. Margin: Entire. Texture, upper and lower surfaces: Smooth, glabrous. Color, upper and lower surfaces: Close to 191A.

*Peduncles*.—Length: About 1 cm. Diameter: About 1.5 mm. Strength: Strong. Angle: About 45° from the stem axis. Texture: Smooth, glabrous. Color: Close to 191B.

*Pedicels*.—Length: About 1 mm. Diameter: About 1 mm. Strength: Strong. Angle: Erect to about 30° from the peduncle axis. Texture: Smooth, glabrous. Color: Close to 191B.

*Reproductive organs*.—Stamens: Quantity per flower: Typically four. Anther shape: Oblong. Anther size: About 0.5 mm by 1.5 mm. Anther color: Close to 166A. Pollen amount: None observed. Pistils: Quantity per flower: One. Pistil length: About 2 mm. Stigma shape: Oblong. Stigma color: Close to 197A. Style length: About 1.7 mm. Style color: Close to 157B. Ovary color: Close to 142B.

*Seed/fruit*.—Seed and fruit development have not been observed.

Disease/pest resistance: Plants of the new *Buddleja* have been not been observed to be resistant to pathogens and pests common to *Buddleja* plants.

Garden performance: Plants of the new *Buddleja* have been observed to have good garden performance and tolerate rain, wind and temperatures ranging from about −25° C. to about 33° C.

It is claimed:

1. A new and distinct *Buddleja* plant named 'Pink Pagoda' as illustrated and described.

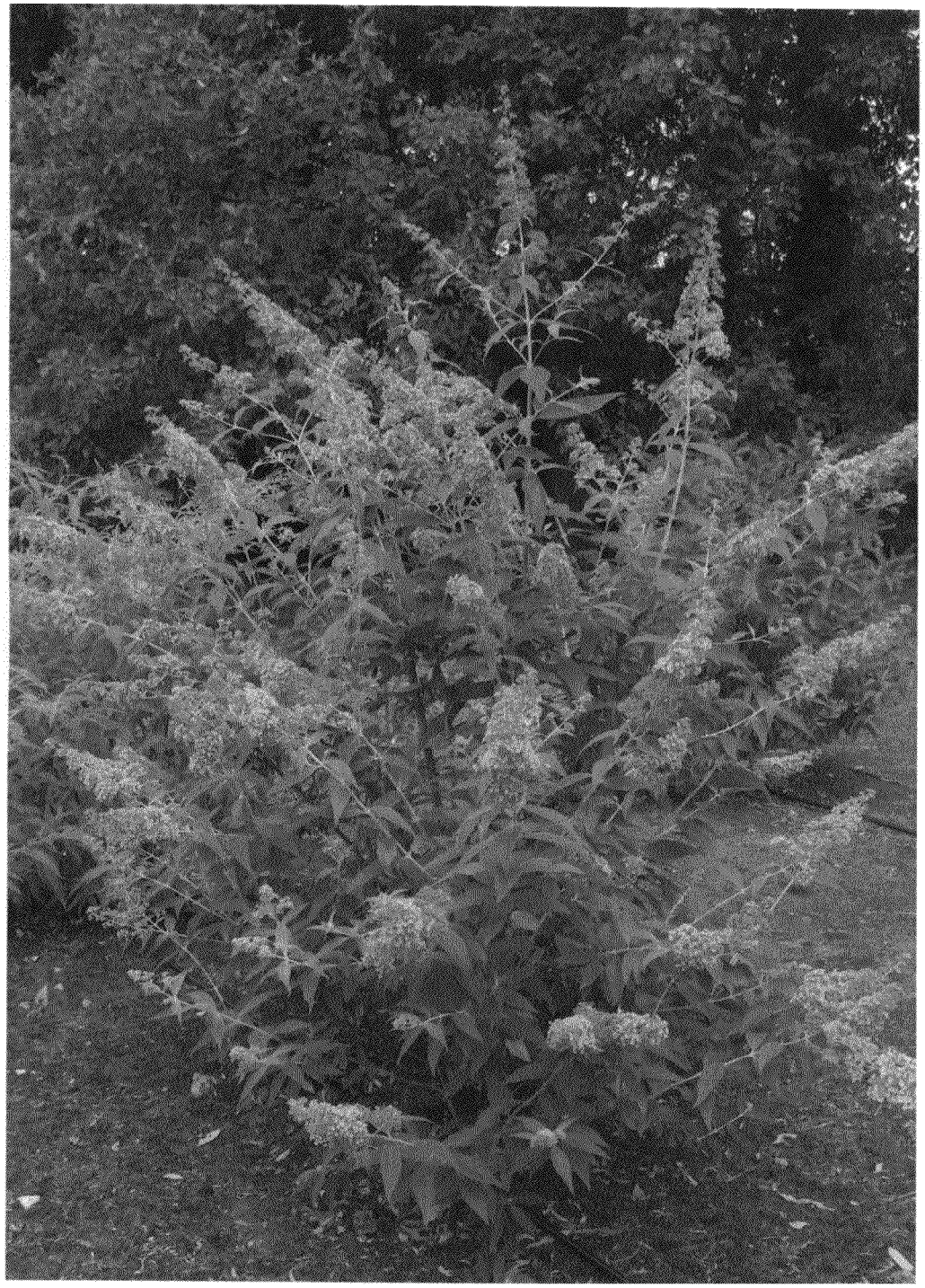

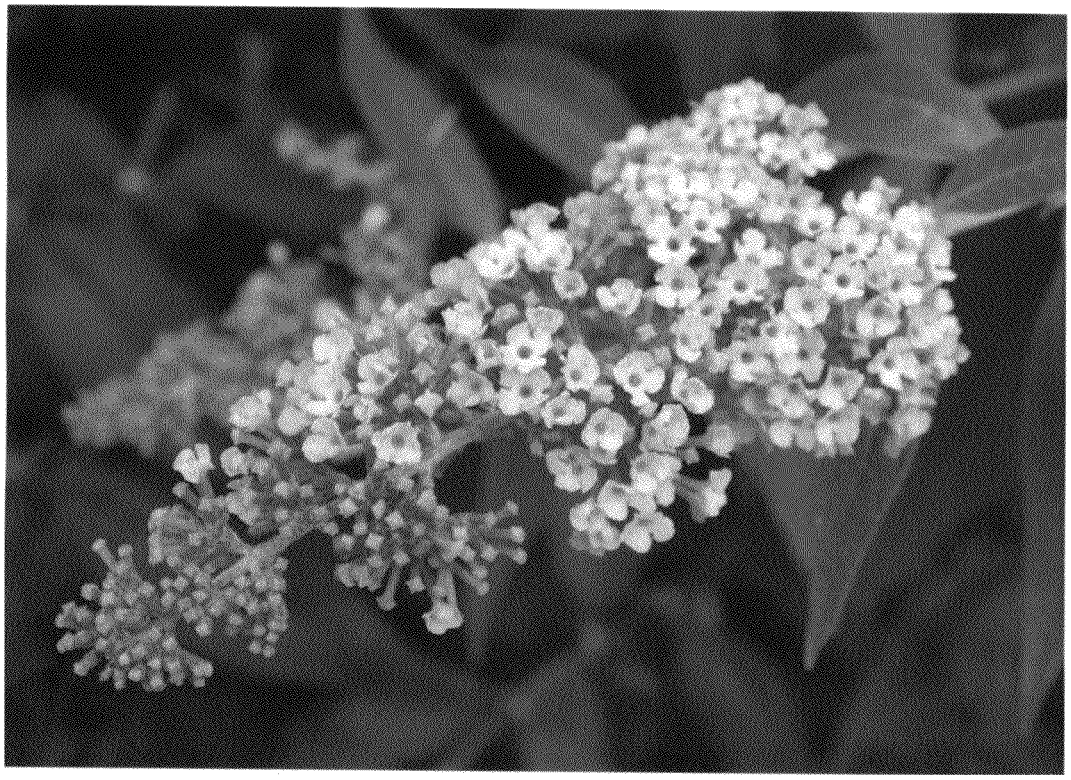

* * * * *